United States Patent [19]

Banks

[11] Patent Number: 5,085,852

[45] Date of Patent: Feb. 4, 1992

[54] ANTIMICROBIAL ORAL COMPOSITIONS

[75] Inventor: Todd J. Banks, West Chester, Ohio

[73] Assignee: The Procter & Gamble Company, Cincinnati, Ohio

[21] Appl. No.: 688,184

[22] Filed: Apr. 19, 1991

[51] Int. Cl.$^5$ .................. A61K 7/16; A61K 7/20; A61K 9/16

[52] U.S. Cl. ...................... 424/53; 424/44; 424/49

[58] Field of Search .................. 424/44, 49–58

[56] References Cited

U.S. PATENT DOCUMENTS

| | | | |
|---|---|---|---|
| 3,518,343 | 6/1970 | Welsh et al. | 424/44 |
| 3,629,468 | 12/1972 | Anderson | 424/44 |
| 3,772,431 | 11/1973 | Mlkvy et al. | 424/44 |
| 3,773,922 | 11/1973 | Gergely | 424/44 |
| 3,882,228 | 5/1975 | Boncey et al. | 424/35 |
| 3,988,433 | 10/1976 | Benedict | 424/53 |
| 4,093,710 | 6/1978 | Sass et al. | 424/44 |
| 4,221,660 | 9/1980 | Eggensperger et al. | 210/764 |
| 4,321,157 | 3/1982 | Harris et al. | 252/174.25 |
| 4,444,674 | 4/1984 | Gray | 252/95 |
| 4,490,269 | 12/1984 | Gallopo | 252/94 |
| 4,670,252 | 6/1987 | Sampathkumar | 424/53 |
| 4,687,662 | 8/1987 | Schobel | 424/44 |
| 4,716,035 | 12/1987 | Sampathkumar | 424/52 |
| 4,886,658 | 12/1989 | Charbonneau et al. | 424/53 |
| 4,917,815 | 4/1990 | Beilfuss et al. | 252/186.23 |
| 4,990,329 | 2/1991 | Sampathkumar | 424/53 |
| 5,015,466 | 5/1991 | Parran et al. | 424/52 |

FOREIGN PATENT DOCUMENTS

| | | |
|---|---|---|
| 66992 | 12/1982 | European Pat. Off. |
| 133354 | 2/1985 | European Pat. Off. |
| 63-020398 | 1/1988 | Japan |
| 63-023996 | 2/1988 | Japan |
| 1477691 | 6/1977 | United Kingdom |
| 2137882A | 10/1984 | United Kingdom |

OTHER PUBLICATIONS

Baldry, M. G. C., "The Antimicrobial Properties of Magnesium Monoperoxyphthlate Hexahydrate", Journal of Applied Bacteriology, vol. 57, pp. 499–503 (1984).

Kao Corp., C.A. 109:8450M (1988), of Jpn. 6302399b (2-1-88).

Primary Examiner—Shep K. Rose
Attorney, Agent, or Firm—Douglas C. Mohl; Kim William Zerby; Richard C. Witte

[57] ABSTRACT

Disclosed are oral compositions useful for treating and/or preventing microbial infections in the oral cavity of humans and/or lower animals in need of such treatment comprising a monoperphthalic acid compound and suitable carrier materials having at least 70% of the particle sizes of the latter component(s) in a range of from about 40 microns to 500 microns.

16 Claims, No Drawings

ANTIMICROBIAL ORAL COMPOSITIONS

BACKGROUND OF THE INVENTION

Many microbial infections arise endogenously. Bacteria and yeast are a part of the normal flora of the skin. They also exist prevalently on all mucous membrane surfaces as indigenous flora. Given the proper circumstances and opportunity to penetrate tissues, bacteria from the indigenous flora can set up infections, such as gas gangrene, vulvovaginal abscess, chronic sinusitis, and Vincent's disease.

While good oral hygiene, as achieved by brushing the teeth with a cleansing dentifrice, may help reduce the incidence of periodontal disease, it does not necessarily prevent or eliminate its occurrence. This is because microorganisms contribute to both the initiation and progress of periodontal disease. Thus, in order to prevent or treat periodontal disease, these micoorganisms must be suppressed by some means other than simple mechanical scrubbing. Towards this end, there has been a great deal of research aimed at developing therapeutic dentifrices, mouthwashes, and methods of treating periodontal disease which are effective in suppressing these microorganisms. Treatment with monoperoxy acid compounds has been suggested in treating microbial infections of the oral cavity.

Monoperoxy acids are known for treating microbial diseases of the oral cavity. U.S. Pat. No. 4,990,329, issued Feb. 5, 1991 to Sampathkumar discloses an oral hygiene composition comprising a monoperphthalic acid compound or its pharmaceutically-acceptable salts or esters. These compositions are used to treat or prevent anaerobic infections in humans and lower animals.

U.S. Pat. No. 4,886,658, issued Dec. 12, 1989 to Charbonneau discloses methods for treating or preventing dental plaque, caries, or gingival or periodontal diseases of the oral cavity in humans or lower animals, with reduced staining of teeth or dentures. Compositions suitable for use in this invention comprise a monoperoxyphthalate compound and an anti-plaque bisbiguanide compound.

U.S. Pat. No. 4,716,035, issued Dec. 29, 1987 to Sampathkumar discloses oral compositions comprising certain organic peroxy acid agents and a source of fluoride ions. These compositions are used as anticaries and antigingivitis agents.

Monoperoxy acids are also used for other disinfecting/cleansing purposes. European Patent Application No 0,133,354 published Feb. 20, 1985 by Interox Chemicals Limited, discloses denture cleansing compositions comprising an organic peroxygen compound, especially in effervescent tablet form.

Great Britain Patent Specification No. 2,137,822A, published Oct. 17, 1984 by Interox Chemicals Limited, discloses an alkanolic solution of a magnesium salt of an aryl, cycloaliphatic, or conjugated aliphatic carboxylic acid (substituted by one or more peroxycarboxylic acid groups). This invention is said to be useful as a broad spectrum disinfectant/sterilizing agent for hard surfaces.

U.S. Pat. No. 4,917,815, issued Apr. 17, 1990 to Beilfuss et al., discloses aqueous solutions of aromatic percarboxylic acids. Uses for this invention include acidic or neutral liquid disinfectants for surfaces with low to medium loading of dirt for the skin, the mucous membranes or the hands.

U.S. Pat. No. 4,490,269 issued Dec. 25, 1984 to Gallopo discloses a denture cleansing composition comprising an effervescent agent, and as a bleaching agent, a monoperphthalate or a potassium monopersulfate and a monoperphthalate.

U.S. Pat. No. 4,221,660, issued Sept. 9, 1980 to Eggensperger et al., discloses a method for disinfecting an aqueous system with a solid aromatic percarboxylic acid having solubility in water. Percarboxylic acids which may be employed in this invention includes monoperphthalic acid.

When a granule oral composition comprising a monoperphthalic acid compound and a suitable carrier material(s) is desired, it is necessary to obtain a homogeneous mix of the monoperphthalic acid compound with the suitable carrier materials. These granule oral compositions of the present invention may be used alone or dissolved in an aqueous medium (e.g. water) and utilized as a mouthrinse or mouth spray for treating or preventing microbial infections in the oral cavity of humans and/or lower animals in need of such treatment. When said granule oral compositions are dissloved in an aqueous medium, a rapid and complete dissolution of the granule monoperphthalic acid compound-containing compositions is necessary to ensure clarity and efficacy of these products.

In spite of the prior disclosures, there remains a need for granule oral compositions comprising a monoperphthalic acid compound and a suitable carrier material(s) which provide a homogeneous mixture and rapid dissolution of these components. Surprisingly, it has been discovered that when the particle sizes of the components of possible suitable carrier materials, are maintained at ranges from about 40 microns to about 500 microns, a homogeneous granule composition is achieved which exhibits rapid dissolution in an aqueous medium.

It is an object of the present invention to provide granule oral compositions for treating and/or preventing microbial infections in the oral cavity of humans and/or lower animals in need of such treatment comprising a monoperphthalic acid compound and a suitable carrier material(s), wherein the particle sizes of the suitable carrier materials(s) are from about 40 microns to about 500 microns.

It is also an object of the present invention to provide a granule oral composition comprising a monoperphthalic acid compound and a suitable carrier material(s) that exhibits a homogeneous mix of ingredients and a rapid dissolution time (from about 15 seconds to about 50 seconds). An additional object of the present invention is to provide methods for treating or preventing microbial infections of the oral cavity by administering to humans or lower animals in need of such treatment an oral composition comprising a monoperphthalic acid compound and a suitable carrier material(s) wherein the particle sizes of the suitable carrier material(s) are from about 40 microns to about 500 microns.

These and other objects of the present invention will be apparent from the detailed description of the invention contained hereinafter.

All percentages and ratios herein are by weight and all measurements are made at 25° C. unless otherwise specified.

SUMMARY OF THE INVENTION

The present invention provides granule oral compositions for treating and/or preventing microbial infections in the oral cavity of a human or lower animal in need of such treatment comprising:
(a) a safe and effective amount of a monoperphthalic acid compound;
(b) a suitable carrier material(s) and
wherein at least 70% of the particle sizes of component(s) (b) are from about 40 microns to about 500 microns.

The present invention further provides for a method for treating and/or preventing microbial infections in the oral cavity of humans and/or lower animals in need of such treatment by administering a composition comprising a monoperphthalic acid compound and a suitable carrier material(s), wherein at least 70% of the particle sizes of the latter component(s) are from about 40 microns to about 500 microns.

A detailed description of the essential and optional components of the present invention are detailed below.

DETAILED DESCRIPTION OF THE INVENTION

Monoperphthalic Acid Compounds:

The present invention relates to granule oral compositions for treating or preventing microbial diseases of the oral cavity, including an overgrowth of yeast, by administering to humans or lower animals a composition comprising a safe and effective amount of a monoperphthalic acid and a suitable carrier material(s). By "diseases of the oral cavity", as used herein, is meant diseases which are initiated and/or perpetuated by bacteria in the oral cavity, and includes such diseases as, for example, periodontal disease, gingivitis, periodontitis, gingivosis, periodontosis, periodontitis complex, and other inflammatory and/or degenerative conditions of the tissues within the oral cavity, plus caries, Vincent's disease, trench mouth, malodor, and yeast overgrowth. Also specifically included are dentoalveolar infectious, dental abscesses (e.g., cellulitis of the jaw; osteomyelitis of the jaw), acute necrotizing ulcerative gingivitis (i.e., Vincent's infection), infectious stomatitis (i.e., acute inflammation of the buccal mucosa), and Noma (i.e., gangrenous stomatitis or cancrum oris). Oral and dental infections are more fully disclosed in Fingold, *Anaerobic Bacteria in Human Diseases*, chapter 4, pp 78-104, and chapter 6, pp 115-154 (Academic Press, Inc., NY, 1977), the disclosures of which are incorporated herein by reference. The method of treatment of the present invention is particularly effective for treating or preventing periodontal disease, gingivitis and/or periodontitis, while lessening the potential for an overgrowth of yeast to occur in the oral cavity.

By "safe and effective amount" as used herein is meant an amount of a monoperphthalic acid compound, or its pharmaceutically-acceptable salt or ester, high enough to significantly positively modify the infection to be treated, but low enough to avoid serious side effects (at a reasonable benefit/risk ratio), within the scope of sound medical judgment. The safe and effective amount of a monoperphthalic acid compound or its pharmaceutically-acceptable salt or ester will vary with the particular infection (e.g., disease of the oral cavity) being treated, the age and physical condition of the patient being treated, the severity of the infection, the duration of treatment, the nature of concurrent therapy, the specific form (i.e., acid, salt, and/or ester) of the monoperphthalic acid employed, and the particular vehicle from which the monoperphthalic acid is applied.

The monoperphthalic acid compounds, useful in this invention are substituted monoperphthalic acids having the general structure:

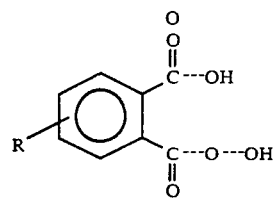

or its pharmaceutically acceptable salts or esters, wherein R may be one or more substituents compatible with the peroxy acid functionality of the aromatic ring.

By "substituents compatible with the peroxy acid functionality of the aromatic ring", as used herein, is meant substituents on the ring which do not react with peroxy acids thereby reducing the stability and effectiveness of the compounds to treat diseases of the oral cavity. Non-limiting examples of R groups include hydrogen, substituted and unsubstituted saturated alkyl having from 1 to about 20 carbon atoms (e.g., methyl, ethyl), substituted and unsubstituted aryl (e.g., phenyl, naphthyl), substituted and unsubstituted benzyl, chloro, fluoro, nitro, sulphonate, trifluoromethyl, trialkylammonium (e.g., trimethylammonium; trethylammonium), cyano, carboxy, carboxylate (e.g., —OCOCH$_3$), percarboxylate (e.g., —CO$_3$H), and alkoxy (e.g., methoxy, ethoxy). Preferred R groups are hydrogen, saturated alkyl having from 1 to about 20 carbon atoms, aryl, benzyl, chloro, fluoro, carboxy, and alkoxy. Particularly preferred for use in the above method for treating or preventing diseases of the oral cavity is monoperphthalic acid (i.e., R=H), or its phamaceutically-acceptable salts or esters. R may also be an iodo, bromo, substituted or unsubstituted amino, or amido group, but such groups are generally not desirable since they can react with peroxy acid groups. Selection of substituents compatible with the peroxy acid functionality of the aromatic ring can easily be made by one skilled in the art.

By "pharmaceutically-acceptable salts or esters", as used herein, is meant esters and salts of the substituted or unsubstituted monoperphthalic acid compounds which have the same general antibacterial properties as the preferred magnesium salt of monoperphthalic acid, and which are acceptable from a toxicity viewpoint. Nonlimiting examples of pharmaceutically-acceptable salts include alkali metal (e.g., sodium, potassium), alkaline earth metal (e.g., calcium, magnesium), non-toxic heavy metal, and trialkyl ammonomium (e.g., trimethylammonium). Preferred compounds for treating or preventing diseases of the oral cavity are pharmaceutically-acceptable salts of the substituted or unsubstituted monoperphthalic acid compounds, with the pharmaceutically-acceptable salts of divalent cations more preferred (e.g., magnesium, calcium) and the magnesium salt being the most preferred.

Most preferred for use in the above method of treating or preventing surface tissue infections caused by or involving microbial organisms, and particularly preferred for diseases of the oral cavity, is the magnesium salt of monoperphthalic acid. This magnesium salt is the salt of the carboxylic acid group only, having the formula:

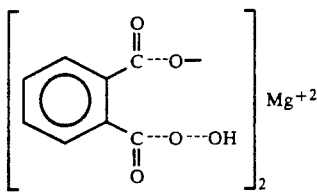

as disclosed in European Patent Application No. 27,693, published Apr. 29, 1981, filed by Interox Chemicals, Ltd., the disclosures of which are incorporated herein by reference. This compound is a hexahydrate when in its solid form.

Synthesis of substituted and unsubstituted monoperphthalic acid compounds can be achieved by those skilled in the art using methods disclosed in, for example, European Patent Application No. 27,693, published Apr. 29, 1981, filed by Interox Chemicals Limited; European Patent Application 66,992, to Interox Chemicals Limited; U.S. Pat. No. 3,075,921, to Brockelhurst et al.; "Organic Peroxides", Daniel Swern, Editor, published 1970 by John Wiley & Sons, Inc.; and in British Patent Specification No. 1,378,671; the disclosures of all of which being incorporated herein by reference. Synthesis of the magnesium salt of monoperphthalic acid is disclosed in the European Patent Application No. 27,693, cited above. This compound is also commercially available from Interox Chemicals Limited.

Granule oral compositions for treating and/or preventing microbial diseases of the oral cavity as defined by the present invention hereinabove, comprise a monoperphthalic acid or its pharmaceutically-acceptable salts or esters in an amount of from about 1.76% to about 55%; a more preferred amount is from about 4.4% to about 22.1%. The most preferred amount of monoperphthalic acid or its pharmaceutically-acceptable salts or esters useful in the present invention is from about 8.8% to about 17.7%.

Suitable Carrier Materials:

Suitable carrier materials for the oral granule compositions of the present invention should be compatible with the monoperphthalic acid and anionic surfactants present in the oral compositions of the present invention. By "compatible", as used herein, is meant that the components of the composition are capable of being commingled without interaction in a manner which would substantially reduce the compositions efficacy for treating or preventing microbial diseases of the oral cavity, according to the method of the present invention.

Examples of suitable carrier materials useful in the granule oral formulations of the present method of treatment or prevention invention include, but are not limited to the group consisting of flavoring agents, sweetening agents (e.g. saccharin, magnasweet), coloring agents, humectants, emulsifying agents, buffering agents, and mixtures thereof.

A buffering agent is useful in this invention to maintain a desirable pH of the monoperphthalic acid/carrier material containing composition of from about 5 to about 7, and preferably from about 5 to about 5.5. Examples of buffering agents useful in the present invention include, but are not limited to sodium bicarbonate, citric acid, malic acid, tartaric acid, gluconic acid and monosodium phosphate. Preferred buffering agents for the present invention are sodium bicarbonate, citric acid, and monosodium phosphate.

Optionally, the oral compositions of the present invention may contain a water-soluble fluoride compound in an amount sufficient to give a fluoride concentration of from about 0.0025% to about 5.0% by weight, preferably from about 0.005% to about 2.0% by weight, to provide anticaries effectiveness. The fluoride compounds are believed to provide protection against demineralization as well as aid in remineralization of dental enamel. Preferred fluorides are sodium fluoride, stannous fluoride, indium fluoride, and sodium monofluorophosphate. Norris et al., U.S. Pat. No. 2,946,725, issued July 26, 1960 and Widder et al., U.S. Pat. No. 3,678,154, issued July 18, 1972 disclose such salts as well as others.

The granular compositions useful in the methods of the present invention comprise a monoperphthalic acid or its pharmaceutically-acceptable salts or esters in an amount of from about 1.76% to about 55%; more preferably from about 4.4% to about 22.1%; most preferably from about 8.8% to about 17.7%; and suitable carrier material(s) in an amount of from about 45% to about 98.24%; more preferably from about 77.9% to about 95.6%; most preferably from about 82.3% to about 91.2%.

It is necessary for the granule oral compositions of the present invention that at least 70% of the particle sizes of the suitable carrier material(s) are from about 40 microns to about 500 microns. It is preferable for the present invention that at least 80% of the particle sizes of the suitable carrier material(s) are from about 80 microns to about 400 microns, and most preferably that at least 95% of these carrier materials are from about 100 microns to about 300 microns.

Typically, the suitable carrier materials are available commercially in the preferred particle size ranges of from about 40 microns to about 500 microns. However certain of the buffering agents (e.g. citric acid, monosodium phosphate, and sodium bicarbonate), which are useful carrier materials in the present invention, are not commonly supplied in the 100 micron to 300 micron particle size range, but may be purchased commercially from specific suppliers. Citric acid is available commercially in the particle size range of from about 50 microns to about 300 microns from Haarmann & Reimer Corporation, Branchburg, N.J.; monosodium phosphate is available commercially in the particle size range of from about 50 microns to about 250 microns from FMC, Philadelphia, Pa.; and sodium bicarbonate is available commercially in the particle size range of from about 88 microns to about 250 microns from Mays Chemical, Indianapolis, Ind.

Method of Treatment:

The method aspect of this invention involves treating and/or preventing microbial diseases of the oral cavity, said method comprising administering to humans or lower animals in need of such treatment or prevention an oral granule composition comprising a monoperphthalic acid compound and a suitable carrier material(s) as described in detail hereinabove.

The granule compositions useful in the methods of the present invention, as described in detail hereinabove may be used in preparing aqueous compositions that may then be useful to treat or prevent microbial infections of the oral cavity, including an overgrowth of yeast, in humans or lower animals in need of such treatment. The aqueous solutions of monoperphthalic acid or its pharmaceutically-acceptable salts or esters and carrier materials are prepared by dissolving the granular compositions, as described in detail hereinabove, in a suitable aqueous medium (such as water or a mixture of water and an alcohol that is proven to be safe for human use) such that the resulting solutions provide monoperphthalic acid or its pharmaceutically-acceptable salts or esters in a range of from about 0.1% to about 5%; more preferably from about 0.25% to about 1.25%; most preferably from about 0.5% to about 1%.

These monoperphthalic acid compound-containing solutions are used in the methods of the present invention to treat or prevent microbial infections of the oral cavity, said methods comprising having a human or lower animal in need of such treatment retain in the oral cavity from about 5 ml to about 30 ml; more preferably from about 10 ml to about 20 ml; most preferably from about 12 ml to about 18 ml of said solutions.

In the methods of the present invention, these granule oral compositions are preferably used from about once to about four times daily, more preferably once or twice daily; most preferably twice daily. The oral compositions in the methods of the present invention are administered by contacting them with the dental surfaces in the oral cavity for from about one second to about 300 seconds during each use, more preferably from about 10 seconds to about 120 seconds during each use, most preferably from about 30 seconds to about 60 seconds during each use.

The following examples further describe and demonstrate preferred embodiments within the scope of the present invention. The examples are given solely for illustration and are not to be construed as limitations of this invention, as many variations thereof are possible without departing from the spirit and scope thereof.

EXAMPLE I

|  | Powder Wt (g) | Wt % in Powder |
|---|---|---|
| PAM$^{(a)}$ | 0.1828 | 20.31% |
| Sodium Bicarbonate | 0.2019 | 22.43% |
| Monosodium Phosphate | 0.1908 | 21.20% |
| Citric Acid | 0.1590 | 17.67% |
| Peppermint | 0.1113 | 12.37% |
| Sodium lauryl sulfate$^{(b)}$ | 0.0159 | 1.77% |
| Saccharin | 0.0286 | 3.18% |
| Magnasweet 100 | 0.0095 | 1.06% |
| FD&C Blue Dye | 0.0002 | 0.02% |
| Total | 0.9000 | 100.0% |

*At least 97% of all particle sizes of the above granular components, except PAM, are within the range of from 100 microns to 300 microns.
$^{(a)}$PAM used in this formulation contains 87% magnesium monoperphthalate and 13% magnesium bis(hydrogen phthalate), sold by Interox Chemicals, Ltd., Warrington, Cheshire, England.
$^{(b)}$sodium lauryl sulfate is sold by Fisher Scientific, Pittsburgh, Pennsylvania.

A human or lower animal in need of a method of treatment of prevention of microbial diseases of the oral cavity places the above powder mixture in 15 ml of water, thereby providing a composition containing 1.0% monoperphthalic acid and 0.1% sodium lauryl sulfate. The human or lower animal then retains and/or swishes the aqueous composition around in the oral cavity for 30-60 seconds.

EXAMPLE II

|  | Powder Wt (g) | Wt % in Powder |
|---|---|---|
| PAM$^{(a)}$ | 0.0908 | 11.35% |
| Sodium Bicarbonate | 0.1971 | 24.64% |
| Monosodium Phosphate | 0.1896 | 23.70% |
| Citric Acid | 0.1580 | 19.75% |
| Peppermint | 0.1106 | 13.82% |
| Sodium lauryl sulfate$^{(b)}$ | 0.0158 | 1.98% |
| Saccharin | 0.0284 | 3.56% |
| Magnasweet 100 | 0.0095 | 1.18% |
| FD&C Blue Dye | 0.0002 | 0.02% |
| Total | 0.8000 | 100.0% |

*At least 97% of all particle sizes of the above granular components, except PAM, are within the range of from 100 microns to 300 microns.
$^{(a)}$PAM used in this formulation contains 87% magnesium monoperphthalate and 13% magnesium bis(hydrogen phthalate), sold by Interox Chemicals, Ltd., Warrington, Cheshire, England.
$^{(b)}$sodium lauryl sulfate is sold by Fisher Scientific of Pittsburgh, Pennsylvania.

A human or lower animal in need of a method of treatment of prevention of microbial diseases of the oral cavity should place the above powder mixture in 15 ml of water, thereby providing a composition containing 0.5% monoperphthalic acid and 0.1% sodium lauryl sulfate. The human or lower animal then retains and/or swishes the aqueous composition around in the oral cavity for 30-60 seconds.

What is claimed is:

1. Granule oral compositions for treating and/or preventing microbial infections in the oral cavity of humans or lower animals in need of such treatment comprising:
   (a) a safe and effective amount of monoperphthalic acid compound; and
   (b) a suitable buffered carrier material(s) comprising
      (i) a soluble bicarbonate salt;
      (ii) a soluble phosphate salt; and
      (iii) citric acid
   wherein at least 70% of the particles of component(s) (b) are from about 40 microns to about 500 microns.

2. Granule oral compositions, according to claim 1, wherein the monoperphthalic acid compound is the magnesium salt of monoperphthalic acid.

3. Granule oral compositions, according to claim 2, wherein additional suitable carrier materials(s) is selected from the group consisting of flavoring agents, sweetening agents, coloring agents, humectants, emulsifying agents, surfactants, abrasives, buffering agents, and mixtures thereof.

4. Granule oral compositions, according to claim 3, wherein at least 80% of the particles of component(s) (b) are from about 80 microns to about 400 microns.

5. Granule oral compositions, according to claim 3, wherein at least 95% of the particles of component(s) (b) are from about 100 microns to about 300 microns.

6. Granule oral compositions for treating and/or preventing microbial infections in the oral cavity of humans or lower animals in need of such treatment comprising:
   (a) from about 1.76% to about 55% of a monoperphthalic acid compound; and
   (b) from about 45% to about 98.24% of a suitable buffered carrier material(s) comprising
      (i) a soluble bicarbonate salt;
      (ii) a soluble phosphate salt; and
      (iii) citric acid wherein at least 70% of the particles of component(s) (b) are from about 40 to about 500 microns.

7. Granule oral compositions, according to claim 6, wherein additional suitable carrier material(s) is selected from the group consisting of flavoring agents, sweetening agents, coloring agents, humectants, emulsifying agents, surfactants, abrasives, buffering agents, and mixtures thereof.

8. A method, for treating and/or preventing microbial infections of the oral cavity of humans, or lower animals in need of such treatment comprising applying to said cavity a composition according to claim 1 which has been dissolved in an aqueous medium.

9. A method, according to claim 7, wherein said composition is retained in the oral cavity for from about 1 second to about 300 seconds.

10. A method, according to claim 7, where said composition is retained in the oral cavity for from about 10 seconds to about 120 seconds.

11. A method, according to claim 7, wherein said composition is retained in the oral cavity for from about 30 seconds to about 60 seconds.

12. A method, for treating and/or preventing microbial infections of the oral cavity of humans, or lower animals in need of such treatment comprising applying to said cavity a composition according to claim 6 which has been dissolved in an aqueous medium.

13. A method, according to claim 12, wherein said composition is retained in the oral cavity for from about one second to about 300 seconds.

14. A method, according to claim 12, wherein said composition is retained in the oral cavity for from about 10 seconds to about 120 seconds.

15. A method, according to claim 12, wherein said composition is retained in the oral cavity for from about 30 seconds to about 60 seconds.

16. A method, according to claim 13, wherein said treatment is retained in the oral cavity for from about 30 seconds to about 60 seconds.

* * * * *